(12) United States Patent
Zand et al.

(10) Patent No.: US 6,559,772 B2
(45) Date of Patent: May 6, 2003

(54) MOISTURE SENSING APPARATUS

(75) Inventors: Farnaz Zand, 212 E. Providencia, Burbank, CA (US) 91502; Warren M. Haussler, Pasadena, CA (US); Robert E. Evans, Sierra Madre, CA (US)

(73) Assignee: Farnaz Zand, Burbank, CA (US)

( * ) Notice: Subject to any disclaimer, the term of this patent is extended or adjusted under 35 U.S.C. 154(b) by 0 days.

(21) Appl. No.: 09/912,577

(22) Filed: Jul. 24, 2001

(65) Prior Publication Data

US 2003/0020615 A1 Jan. 30, 2003

(51) Int. Cl.[7] .............................................. G08B 21/00
(52) U.S. Cl. ...................... 340/604; 340/573.1; 604/361
(58) Field of Search ................................. 340/604, 605, 340/573.1; 128/886; 604/361

(56) References Cited

U.S. PATENT DOCUMENTS

| | | | |
|---|---|---|---|
| 3,939,360 A | 2/1976 | Jackson | 307/118 |
| 4,106,001 A | 8/1978 | Mahoney | 128/886 |
| 4,191,950 A | 3/1980 | Levin et al. | 340/604 |
| 4,212,295 A | 7/1980 | Snyder | 307/118 |
| 4,347,503 A | 8/1982 | Uyehara | 340/604 |
| 4,356,818 A | 11/1982 | Macias et al. | 128/886 |
| 4,484,573 A | 11/1984 | Yoo | 340/604 |
| 4,539,559 A | 9/1985 | Kelly et al. | 340/604 |
| 5,036,859 A * | 8/1991 | Brown | 128/734 |
| 5,226,386 A | 7/1993 | Thoma | 340/604 |
| 5,266,928 A * | 11/1993 | Johnson | 340/604 |
| 5,557,263 A * | 9/1996 | Fisher et al. | 340/605 |
| 5,760,694 A * | 6/1998 | Nissim et al. | 340/604 |
| 5,790,036 A * | 8/1998 | Fisher et al. | 340/605 |
| 5,817,081 A | 10/1998 | LaVon et al. | 340/573.1 |
| 5,838,240 A * | 11/1998 | Johnson | 340/604 |
| 5,908,411 A * | 6/1999 | Matsunari | 604/361 |
| 6,091,336 A | 7/2000 | Zand et al. | 340/604 |
| 6,097,297 A * | 8/2000 | Fard | 340/604 |
| 6,163,262 A * | 12/2000 | Wu | 340/604 |
| 6,200,250 B1 * | 3/2001 | Janzen | 493/383 |
| 6,246,330 B1 * | 6/2001 | Nielsen | 340/604 |

* cited by examiner

Primary Examiner—Toan Pham
(74) Attorney, Agent, or Firm—Fulbright & Jaworski L.L.P.

(57) ABSTRACT

An apparatus for sensing moisture in a diaper comprises a portable alarm unit, a pouch-like diaper insert made from waterproof dental bib material with an opening at one end and a moisture sensing strip made of highly efficient liquid absorption and transfer capillary wick material. The wick strip has a substantially short front non-conductive portion protruding out of the diaper insert for placement in a diaper crotch area and a substantially long back portion having a pair of screen-printed spaced apart conductive ink bands which couple electrically at one end to the alarm unit. The conductive ink bands include a terminal tortuous conductive ink pattern screen-printed in close proximity to the substantially short first wick portion to increase moisture contact surface area, minimize moisture transfer distance and significantly reduce the alarm unit response time.

11 Claims, 10 Drawing Sheets

MOISTURE SENSING APPARATUS

BACKGROUND OF THE INVENTION

1. Field of the Invention

The present invention relates generally to moisture sensing devices and more particularly to an apparatus for sensing urination in clothing articles such as diapers worn by young children and/or incontinent adults, respectively, and for emitting alarm signal(s) to alert a caregiver that a diaper change is needed.

2. Prior Art

Bladder incontinence is a problem endemic in the very young and is cured only by intensive training as the young child goes through its second and third year of life requiring in the meantime the constant use of diapers. The same problem can affect the elderly or the infirm or persons of any age who may have this problem because of physiological or psychological problems. A problem of this nature may be a major source of embarrassment. The mere fear of such incontinence can be a danger to the psychological welfare of persons already subject to severe psychological pressures due to other infirmities. Such people, both the very young and the infirm often have no warning that their undergarments are being wet by urine until the undergarments are uncomfortably wet. There has always been a need for a device which can automatically warn either the person involved, or his/her caretaker (nurse or parent) that such undesirable leakage or wetness has occurred.

Various devices for detecting moisture or wetness such as caused by urination are known in the prior art. In diapers, the purpose of such devices is to set off an alarm when the diaper becomes wet. This permits a parent or other attendant to immediately tend to a newborn infant, toddler or an incontinent adult. Such devices usually include a pair of electrodes placed in the diaper which conduct electric current if wetness is detected. Prior art devices of this type, however, have numerous disadvantages such as requiring current-carrying conductors to pass mechanically through the diaper's plastic outer sheath, may subject the skin of the child/incontinent adult to potentially high voltages, may be sensitive only in a limited area in the diaper, may accidentally respond to the wearer sitting on a wet or metal bench or park slide or may have other undesirable drawbacks.

Urine is a solution of among other things, electrolytes, and will conduct a current of electricity. However, there are serious dangers involved in the use of electrical devices which use this property to sound an alarm. Fail-safe circuitry is a positive must, or there is serious danger of bodily harm.

In the past several years, portable devices have been proposed which have an electrode-containing pad disposed in the groin area of a user. A conductive path is established between the electrodes upon urination and an alarm of some kind is activated. These devices usually respond to urination in a relatively long interval of time (5–15 minutes) and are to a large extent impractical nowadays due to the advent of diapers filled with superabsorbent fill materials derived from a family of hydrophilic polymers known as polyacrylates. The simplest of these substances is sodium polyacrylate which can hold 800 times its weight in distilled water. Urine contains not only water but also dissolved salts and ions which reduce the absorbency of these materials only by a factor of 10. Some leading brands of diapers use combinations of polyacrylates that can absorb up to 1500 times their weight in water. The competition that these superabsorbent materials present to known moisture detecting devices is enormous. There seems to be insufficient pooling of urine in the diaper which constantly interferes with the operation of these devices.

Known moisture detecting devices also suffer from a number of disadvantages. For example, some devices have been less than completely acceptable to many children because of the bulkiness of the devices in the groin area. Also, some prior devices employ a long and rather stiff electrical cord coupled between a urine sensing pad in the groin area and an alarm unit on the wrist or shoulder of the user. Another disadvantage of such devices is the use of a relatively small urine sensor in the user's groin area. Such relatively small sensors are frequently missed by the flow of urine and fail to trigger the alarm.

A known moisture detecting device attempted to solve the superabsorbent diaper fill problem by using a capillary strip placed in the crotch area of the diaper and a pair of integrated electrical wires (electrodes) placed at the waistline of the diaper and connected to a portable electronic alarm unit. However, placing the electrodes so far away from the crotch area of the diaper resulted in a rather long alarm unit response time (up to 10 minutes). Specifically, device response was dependent on the amount and duration of urination since the liquid transfer distance from the tip of the capillary strip in the crotch area of the diaper to the electrodes at the waistline of the diaper was too long—it extended along the entire width of the diaper.

Therefore, the need arises for an improved device for sensing moisture from urination in an undergarment such as a diaper which can quickly and efficiently sense any available amount of urine present in the diaper crotch area regardless of the duration and amount of urination and which can trigger an associated alarm unit not in a matter of minutes but in a matter of a few seconds.

SUMMARY OF THE INVENTION

The present invention is directed to an apparatus for sensing moisture at a first location which comprises a strip of material adapted to efficiently absorb and transfer moisture via capillary attraction from the first location to a second location disposed in close proximity to the first location, and means for quickly sensing transferred moisture at the second location and triggering a corresponding alarm signal.

In accordance with one aspect of the present invention, the strip of material is made of a highly efficient capillary liquid transfer wick material.

In accordance with another aspect of the present invention, the wick strip comprises a substantially short first portion disposed at the first location, a substantially long second portion disposed adjacent the substantially short first portion and a third portion disposed adjacent the second portion.

In accordance with still another aspect of the present invention, the quick moisture sensing means includes at least two spaced apart conductive ink bands screen-printed on a first side of the second and third portions of the wick strip, a waterproof pouch for enclosing the second portion, and an alarm signaling circuit operatively coupled to the conductive ink bands on the third portion. The waterproof pouch comprises an opening at a first end and a pocket at a second end for removably receiving a portable alarm unit containing the alarm signaling circuit, the substantially short first portion of the wick strip protruding from the first end.

In accordance with yet another aspect of the present invention, the moisture sensing apparatus of the present invention further comprises means for increasing the moisture contact surface area at the second location. The moisture contact surface area increasing means includes a terminal tortuous conductive ink pattern screen-printed on the first side of the second portion in close proximity to the substantially short first portion.

In accordance with a further aspect of the present invention, the waterproof pouch is adapted for coupling to a clothing article on which the first location is defined.

In accordance with an alternative aspect of the present invention, the wick strip comprises a substantially short first portion disposed at the first location, a second portion disposed adjacent the substantially short first portion and a substantially long third portion disposed adjacent the second portion.

In accordance with another alternative aspect of the present invention, the quick moisture sensing means includes at least two spaced apart conductive ink bands screen-printed on a first side of the substantially long third portion of the wick strip, a tortuous conductive ink pattern screen-printed on the first side of the second portion of the wick strip in close proximity to the substantially short first portion, a pouch for waterproofing at least the second portion, and an alarm signaling circuit operatively coupled to the conductive ink bands on the third portion. The pouch comprises an opening at a first end with the substantially short first portion of the wick strip protruding from the first end. The pouch and the third portion of the wick strip are adapted for integrating with a clothing article on which the first location is defined.

In accordance with still another alternative aspect of the present invention, the clothing article is adapted to receive a disposable alarm unit containing the alarm signaling circuit.

In accordance with yet another alternative aspect of the present invention, the clothing article is adapted to receive a reusable alarm unit containing the alarm signaling circuit.

In accordance with a different aspect of the present invention, a method for quickly sensing moisture from urination in a diaper is disclosed. The method comprises the steps of: (a) screen-printing a pair of spaced apart conductive ink bands with a terminal tortuous conductive ink pattern on a strip of highly efficient capillary liquid transfer wick material leaving a substantially short non-conductive front wick portion in close proximity to the tortuous conductive ink pattern; (b) providing a pouch adapted to waterproof at least the tortuous conductive ink pattern portion of the wick strip; (c) operatively coupling an alarm signaling circuit to the screen-printed conductive ink bands on the wick strip; and (d) disposing the substantially short non-conductive front wick portion in a diaper crotch area.

These and other aspects of the present invention will become apparent from a review of the accompanying drawings and the following detailed description of the preferred embodiments of the present invention.

BRIEF DESCRIPTION OF THE DRAWINGS

The invention is generally shown by way of example in the accompanying drawings in which.

DETAILED DESCRIPTION OF THE PREFERRED EMBODIMENTS

Hereinafter, some preferred embodiments of the present invention will be described in detail with reference to the related drawings of FIGS. 1–11. Additional embodiments, features and/or advantages of the invention will become apparent from the ensuing description or may be learned by the practice of the invention.

In the figures, the drawings are not to scale and reference numerals indicate the various features of the invention, like numerals referring to like features throughout both the drawings and the description.

The following description includes the best mode presently contemplated for carrying out the invention. This description is not to be taken in a limiting sense, but is made merely for the purpose of describing the general principles of the invention.

Figure 1:
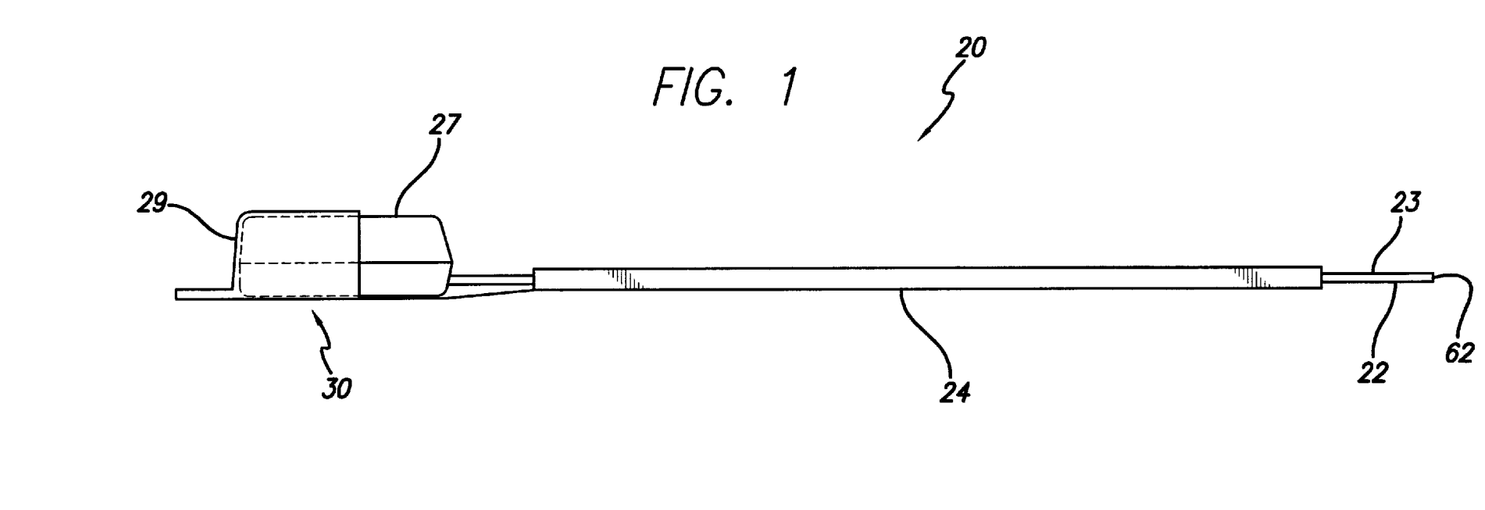
FIG. 1 is a side elevational view of a moisture sensing apparatus in accordance with the present invention.
Figure 2:
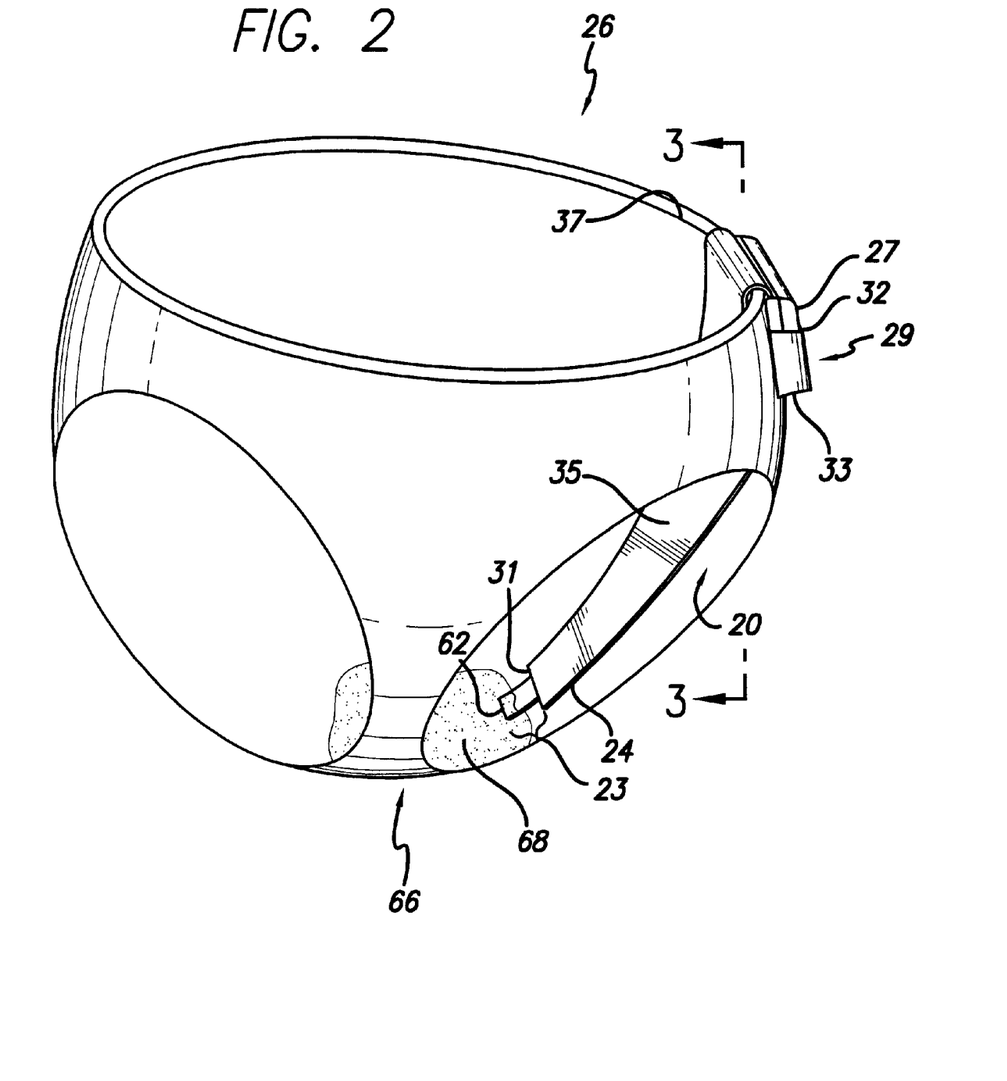
FIG. 2 is a perspective view of an undergarment (such as a diaper) with the moisture sensing apparatus of FIG. 1 applied to the undergarment in accordance with the present invention.
Figure 3:
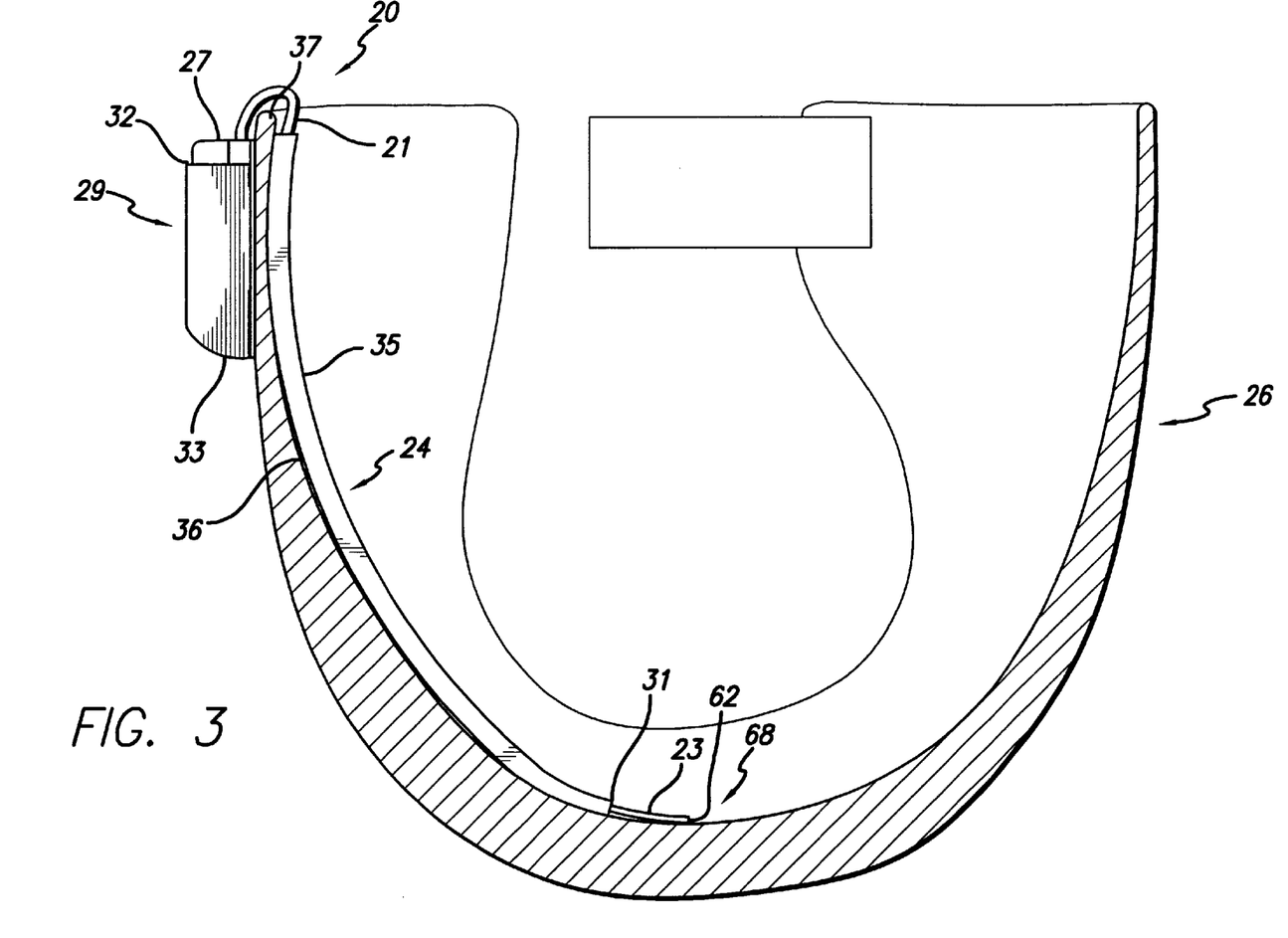
FIG. 3 is a cross-sectional view taken along section line 3—3 of FIG. 2.
Figure 5:
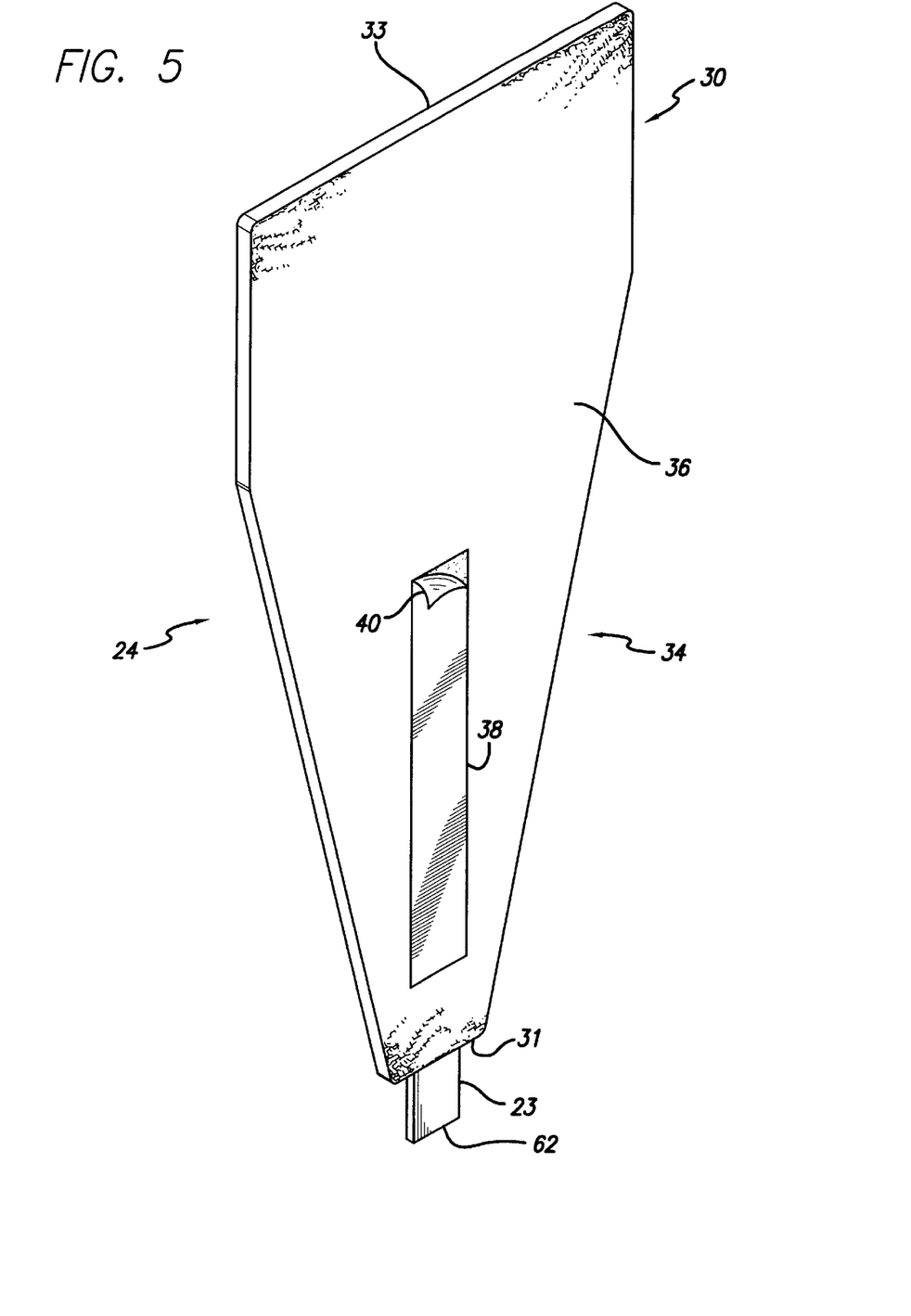
FIG. 5 is a back perspective view of a diaper insert partially enclosing a moisture sensor in accordance with the present invention.

The present invention is directed to a moisture sensing apparatus for use in detection of urination in clothing articles such as diapers for young children and/or incontinent adults, generally referred to by a reference numeral 20, which comprises a disposable pouch-like diaper insert 24 partially enclosing a disposable moisture sensor 22 constructed in accordance with the general principles of the present invention as generally shown in FIG. 1. Diaper insert 24 is preferably designed to be waterproof on the inside, i.e. around the enclosed portion of moisture sensor 22, and is adapted on one side to be adhesively affixed to the inside of a young child's or an incontinent adult's diaper 26 (FIGS. 2, 3, 5). Moisture sensing apparatus 20 is preferably manufactured of low cost materials so as to be used only once and disposed with the diaper.

Figures 6, 7:
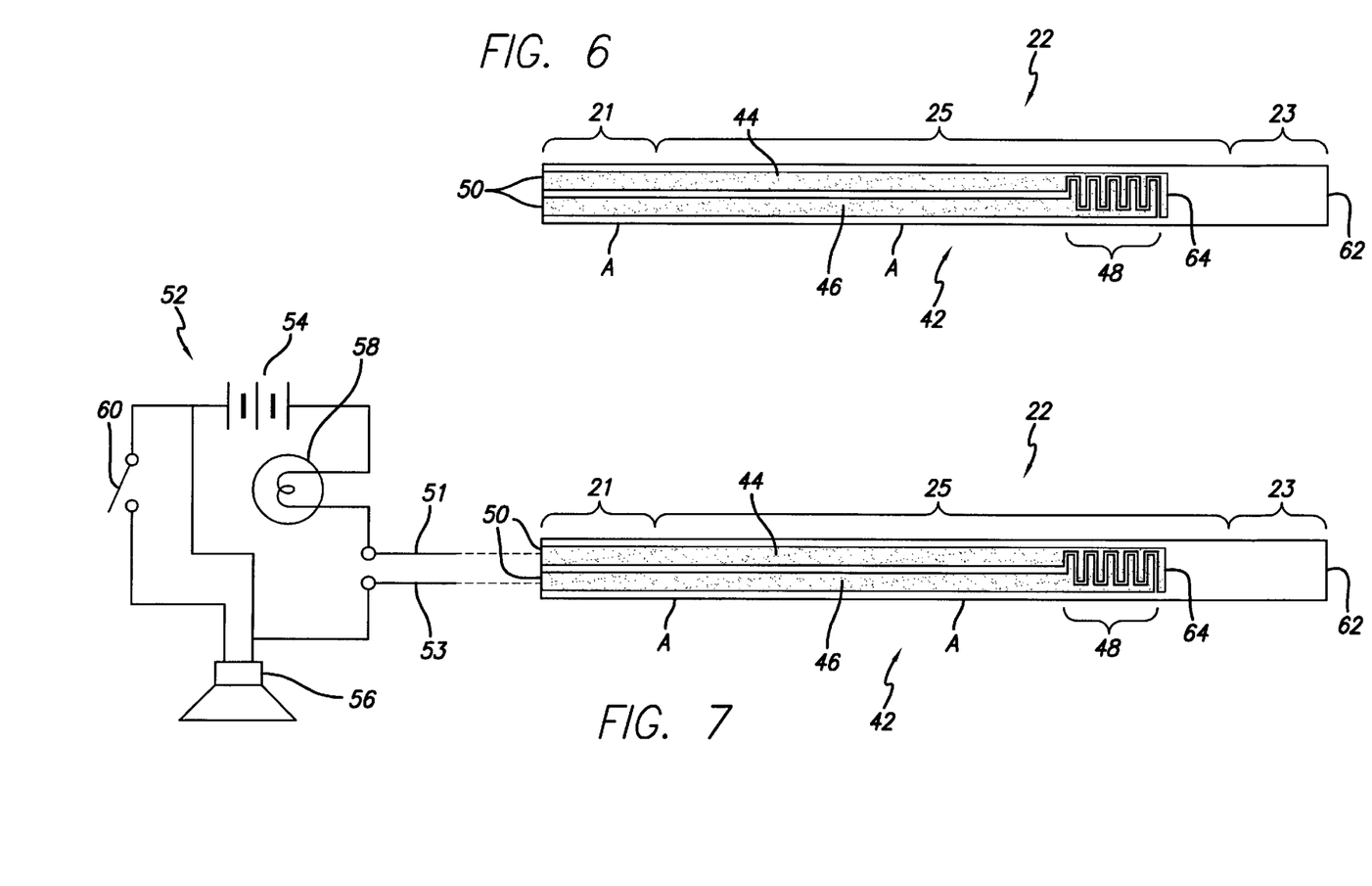
FIG. 6 is a top view of a moisture sensor in accordance with the present invention.
FIG. 7 is a schematic view of the moisture sensor of FIG. 6 shown coupled to an electrical circuit in accordance with the present invention.

In accordance with a preferred embodiment of the present invention, disposable moisture sensor 22 may be constructed from an elongated generally rectangular strip of a highly efficient capillary liquid transfer wick material 42 designed to enhance absorption, retention and transfer of liquid by capillary attraction as shown generally in FIG. 6. A wick of this type may be purchased, for example, from Filtrona Richmond, Inc. of Richmond, Va. under the trademark name TRANSPAD®. TRANSPAD® wicks are designed with high capillarity to enhance liquid transfer, maximize absorptive capacity and are known to have low protein binding and highly uniform liquid flow characteristics which are well suited for sensing minute amounts of liquid reagents such as urine. TRANSPAD® wicks are typically custom made from bonded cellulose acetate fibers aligned parallel to the major (longitudinal) axis (not shown) of the wick to maximize liquid transfer by capillary attraction with the fiber density adjusted by the wick manufacturer according to application so as to optimize wick performance. In general, TRANSPAD® wick thickness varies from 0.03 inch–0.74 inch depending on specific application.

Wick strip 42 comprises a substantially short first portion 23 (FIGS. 1–8) which protrudes out of a first open end 31 (FIGS. 4, 5) of diaper insert 24 and is intended for placement in the crotch area of young child's or incontinent adult's diaper 26 (FIGS. 2, 3) to allow rapid transfer of moisture (such as from urination) by capillary attraction to an adjacent substantially long second portion 25 (FIGS. 6, 7). In one example, first portion 23 may be approximately ≦0.75 inch long. Second portion 25 is preferably fully enclosed by the waterproof inner walls of diaper insert 24 to prevent loss of transferred (from first portion 23) urination to the diaper padding. Second portion 25 is also adapted on a side A (FIGS. 6, 7) to conduct current in the presence of transferred moisture (urination) from the crotch area of the diaper. Wick strip 42 further comprises a third portion 21 (FIGS. 6, 7) disposed adjacent to second portion 25 which is also adapted on side A to conduct current. Third portion 21 protrudes out of diaper insert 24 (FIG. 4) to allow for electrical coupling at an end 50 (FIGS. 6, 7) to an electrical circuit 52 (FIGS. 6, 7) which is part of a relatively compact portable and preferably re-usable alarm signal unit 27 (FIG. 1).

In one example, a TRANSPAD® wick 42 having a length of about 7.75 inch, a width of about 0.5 inch and a thickness of about 0.063 inch may be used to practice the invention. Other wick sizes as well as other types of capillary liquid transfer materials may be utilized to practice the present invention as long as there is no departure from the intended purpose and scope of the present invention.

Alarm Signal unit 27 contains a custom-made electronic circuit board (not shown) adapted to provide light and/or sound and/or vibratory alarm signals or the like to alert a caregiver that a young child or incontinent adult is in need of a diaper change. Alarm signal unit 27 may also be adapted to send a radio signal to a receiver on a remote caregiver.

In another preferred embodiment of the present invention, re-usable alarm signal unit 27 is removably coupled to diaper insert 24 by manually inserting alarm signal unit 27 in a pocket 29 formed in a tail portion 30 of diaper insert 24 (FIG. 1). Other means of coupling alarm signal unit 27 to moisture sensor 22 may be utilized, as long as such other coupling means fall within the scope of the present invention. In one example, portable alarm signal unit 27 may have the following approximate exterior dimensions: 1.5 inch length by 1.4 inch width by 0.2 inch thickness and may be powered by a small 3-volt battery (not shown).

Wick strip 42 is preferably adhesively attached at an opposite side B (FIG. 4) to a waterproof inner wall 70 (FIG. 8) of diaper insert 24. Inner wall 70 may be in the form of a plastic inner backing which generally conforms to the overall shape of diaper insert 24. Other means of securing wick 42 inside diaper insert 24 may be used, provided such other securing means agree with the intended purpose of the present invention.

Figure 4:
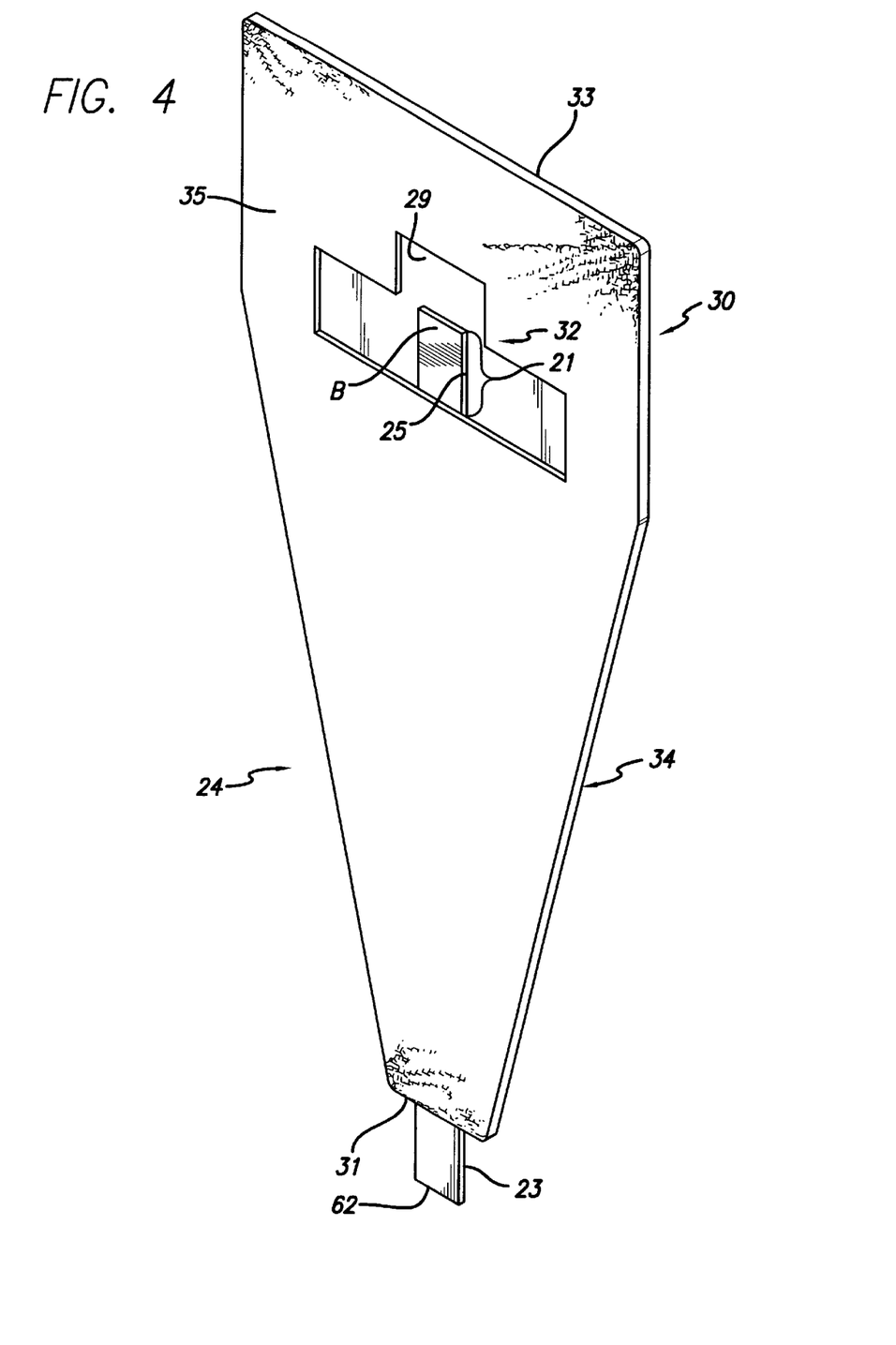
FIG. 4 is a front perspective view of a diaper insert partially enclosing a moisture sensor in accordance with the present invention.
Figure 8:
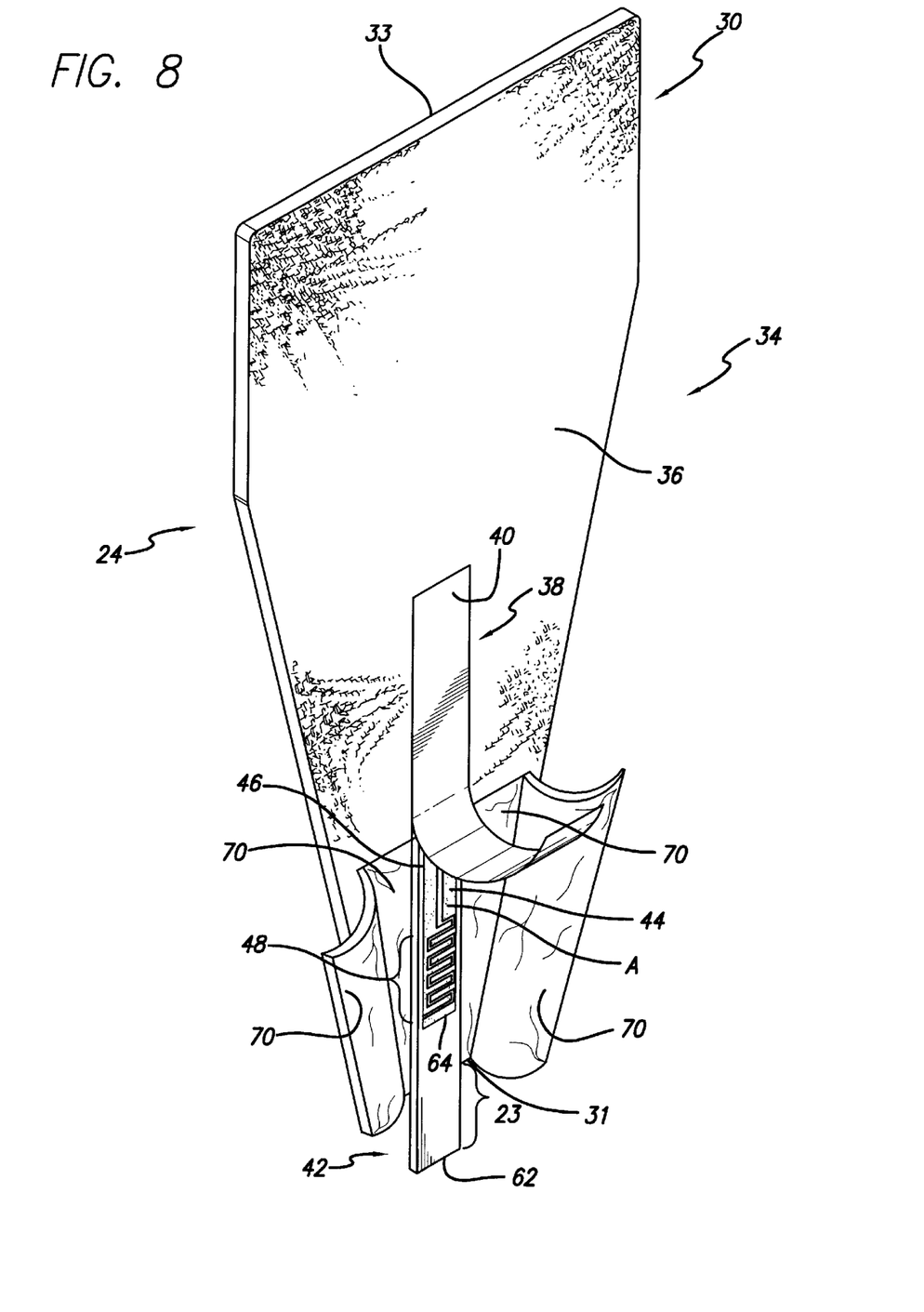
FIG. 8 is a partially cut away back perspective view of a diaper insert enclosing a moisture sensor in accordance with the present invention.

Diaper insert 24 is preferably made from at least one layer of thin flexible material reinforced with a waterproof plastic backing layer on one side which, in one embodiment of the present invention, is cut, folded substantially in the middle such that the waterproof plastic backing remains on the inside to form inner wall 70 (FIG. 8) and then heat-sealed at the open edges on each of two opposing sides to form a relatively flat elongated pouch or envelope which is open at first end 31 (FIGS. 4, 5, 8). Pouch-like diaper insert 24 may be constructed from dental bib-type paper which is usually reinforced on one side with a thin plastic waterproof backing material. Dental-bib type paper may be purchased from medical/dental suppliers such as Henry Schein, Inc. of Melville, N.Y. Providing waterproof plastic inner wall 70 on diaper insert 24 (FIG. 8) helps prevent loss of transferred moisture (from urination) to the paper walls of the diaper insert itself and/or the padding material of the diaper. Other materials suitable for constructing diaper insert 24 may be used provided such other materials fall within the scope of the present invention. One example of such other material is sanitary napkin-type material which is commercially available from Pearson Dental of Sylmar, Calif.

As generally illustrated in FIGS. 4–5, tail portion 30 of pouch-like diaper insert 24 is generally rectangular-shaped, closed at a second end 33 (since end 33 represents the line of folding the dental bib material to form diaper insert 24) and provided on a side 35 with a polygonal cutout 32 to allow third portion 21 of wick strip 42 to electrically couple with electrical circuit 52 (FIG. 7) of alarm signal unit 27. Cutout 32 also serves as the opening for pocket 29 (FIG. 1) of tail portion 30 of diaper insert 24. Tail portion 30 preferably folds over a diaper waistline 37 (FIGS. 2, 3) to form pocket 29 on the outside of diaper 26 for inserting alarm signal unit 27.

A remaining portion 34 of diaper insert 24 is generally trapezoidal-shaped, open at first end 31 (FIGS. 4, 5, 8) to accommodate outwardly protruding substantially short first portion 23 of wick strip 42 and preferably provided at an opposite side 36 (FIG. 5) with a double-sided adhesive strip 38 which has a peelable backing 40 (FIG. 5). Backing 40 is peeled off by the caregiver to adhesively attach side 36 of diaper insert 24 to the inside of diaper 26 (FIGS. 2, 3) such that first portion 23 of wick strip 42 is preferably disposed in the diaper crotch area (FIGS. 2, 3) before the diaper can be used by a young child or an incontinent adult. Other means attaching diaper insert 24 to the inside of diaper 26 may be used such as sewing, laminating in place or the like, provided such other attachment means fall within the scope of the present invention.

In accordance with still another preferred embodiment of the present invention, side A of second and third portions of wick strip 42 is adapted to conduct electric current by screen-printing on it a pair of elongated, spaced apart and generally parallel conductive ink bands 44, 46 as generally depicted in FIGS. 6–8. Conductive ink bands 44, 46 are substantially identical, i.e. of the same width, length and overall configuration. The preferred spacing between conductive ink bands 44, 46 is about one half the width of a conductive ink band (44 or 46).

Conductive ink is formed by mixing carbon powder or silver powder with acrylic resin and solvent and then dispersing the same. Conductive ink may be applied to a variety of substrates by screen printing, dipping and syringe dispensing. Conductive ink suitable for practicing the invention may be purchased, for example, from Creative Materials Incorporated of Tyngsboro, Mass. The preferred thickness of each conductive band (44, 46) is about 0.002 inch–0.003 inch.

In accordance with yet another preferred embodiment of the present invention, conductive ink bands 44, 46 terminate at one end with a tortuous conductive ink pattern 48, one example of which is shown in FIGS. 6–8, designed to increase the moisture contact surface area. Tortuous conductive ink pattern 48 has a front end 64 (FIGS. 6, 7) preferably disposed in close proximity to substantially short first portion 23. In one example, the distance moisture (urination) has to travel by capillary attraction between front end 64 and first portion 23 may be ≦0.75 inch. At the opposite end, conductive ink bands 44, 46 extend all the way to end 50 of third portion 21 of wick strip 42 (FIGS. 6, 7) to couple electrically to leads 51, 53 of electrical circuit 52 (FIG. 7). A person skilled in the art would readily recognize that various other conductive ink patterns may be implemented in lieu of tortuous conductive ink pattern 48 to increase moisture contact surface area in close proximity to substantially short first portion 23 (which is placed in the crotch area of diaper 26), provided such other patterns fall within the scope of the present invention.

Electrical circuit 52 (FIG. 7) is shown as a simplified circuit including a power source or battery 54, an audio alarm device 56, a visual alarm (e.g., colored lights) device 58 and a manual switch 60. Circuit 52 may be disposed in a light-weight plastic housing (not shown) to form a portable alarm signal unit. A person skilled in the art would appreciate that other types of alarm devices may be connected to simplified circuit 52, e.g. a vibratory alarm device or the like. Simplified circuit 52 is merely one example of an electrical circuit which may be used to practice the present invention. Other more complex circuits may be utilized depending on the needs of the caregiver providing such circuits do not deviate from the intended purpose of the present invention.

In accordance with the general principles of the present invention and assuming manual switch 60 in simplified electrical circuit 52 (FIG. 7) is closed, any amount of moisture (from urination) 68 (FIG. 2) in crotch area 66 of diaper 26 coming in contact with a tip 62 (FIG. 2) of first portion 23 of wick strip 42 is being quickly transferred up (via the highly efficient wick strip material 42) to tortuous conductive ink pattern 48 of second portion 25 by capillary attraction. Transferred moisture (from crotch area 66) coming in contact with tortuous conductive ink pattern 48 will short circuit the conductive ink bands 44, 46 (i.e. close circuit 52) triggering alarm devices 56, 58 so as to alert the caregiver that a diaper change is required. A person skilled in the art would readily appreciate that the distance moisture 68 travels to reach tortuous conductive ink pattern 48, which in the above example is about ≦1.5 inch, is substantially shorter than the distance moisture has to travel in the above-described prior art moisture detecting device which used a capillary strip placed in the diaper crotch area and integrated electrical wires (electrodes) disposed far away at the waistline of the diaper. Obviously, substantially shortening the moisture transfer distance, using a highly efficient capillary transfer material, providing a tortuous conductive ink pattern in close proximity to the portion of capillary transfer material disposed in the crotch area of the diaper and wrapping the conductive ink portion with a waterproof layer would lead to a much shorter alarm unit response time. In this regard, a moisture sensing test was conducted by Applicants during development of the moisture sensing apparatus of the present invention as follows:

MOISTURE SENSING TEST—First portion 23 of a TRANSPAD® wick strip was disposed in the crotch area of a diaper with third portion 21 (FIG. 6) electrically coupled to a portable alarm signal unit such as alarm signal unit 27 (FIG. 1). Urination was simulated using 3 oz. of salt water dispensed from a syringe onto the crotch area of a diaper (which was formed and placed in a typical sitting position) where tip 62 of first portion 23 was placed in contact with the diaper (superabsorbent fill) material over a period of 15 seconds. The alarm signal activated within 5 seconds from the start of dispensing, i.e. well before all of the salt water was dispensed.

A person skilled in the art would readily appreciate that providing waterproof plastic inner wall 70 on diaper insert 24 (FIG. 8) helps prevent loss of transferred moisture (from urination) to the paper walls of the diaper insert itself and the padding material of the diaper.

In one example and in accordance with the general principles of the present invention, typical potential and current conducted between conductive ink bands 44, 46 may be about 3 volts and a few microamperes, respectively, i.e. novel moisture sensing apparatus 20 eliminates all of the above-mentioned prior art health safety concerns.

Screen-printing two spaced apart conductive ink bands directly on wick strip 42 instead of attaching or incorporating two plain electrical wires on wick strip 42 reduces the overall cost of the moisture sensing apparatus and provides additional advantages such as using lower potentials, conducting very low currents and the like. The screen-printed conductive ink bands are flexible electrical conductors with a larger overall surface current area than plain electrical wires and are also less likely to be damaged during use alleviating any potential safety concerns a caregiver or user may have.

In general, the shorter first TRANSPAD® wick portion 23 is and the closer a waterproof covered tortuous conductive ink pattern 48 is placed to first TRANSPAD® wick portion 23, the less distance moisture from urination 68 (FIG. 2) has to travel by capillary attraction until it short circuits conductive bands 44, 46 and activates alarm signal unit 27 which makes the concerns of prior art moisture detecting devices about the amount or duration of urination in the diaper largely irrelevant. Also, as shown by Applicants during testing, the moisture sensing apparatus of the present invention substantially moves forward the alarm signal unit response time from a matter of minutes to a matter of seconds which is a significant advantage over known moisture detection devices.

Moisture sensing apparatus 20 may be mass-produced and sold as a disposable device for use with diapers for young children or incontinent adults with alarm signal unit 27 intended to be a re-usable unit with an inexpensive long-lasting battery and an appropriate conductive ink band connector interface which may include a mechanical clamp (not shown). The moisture sending apparatus of the present invention may be used with any diaper without modifying the diaper in any way.

Figure 11:
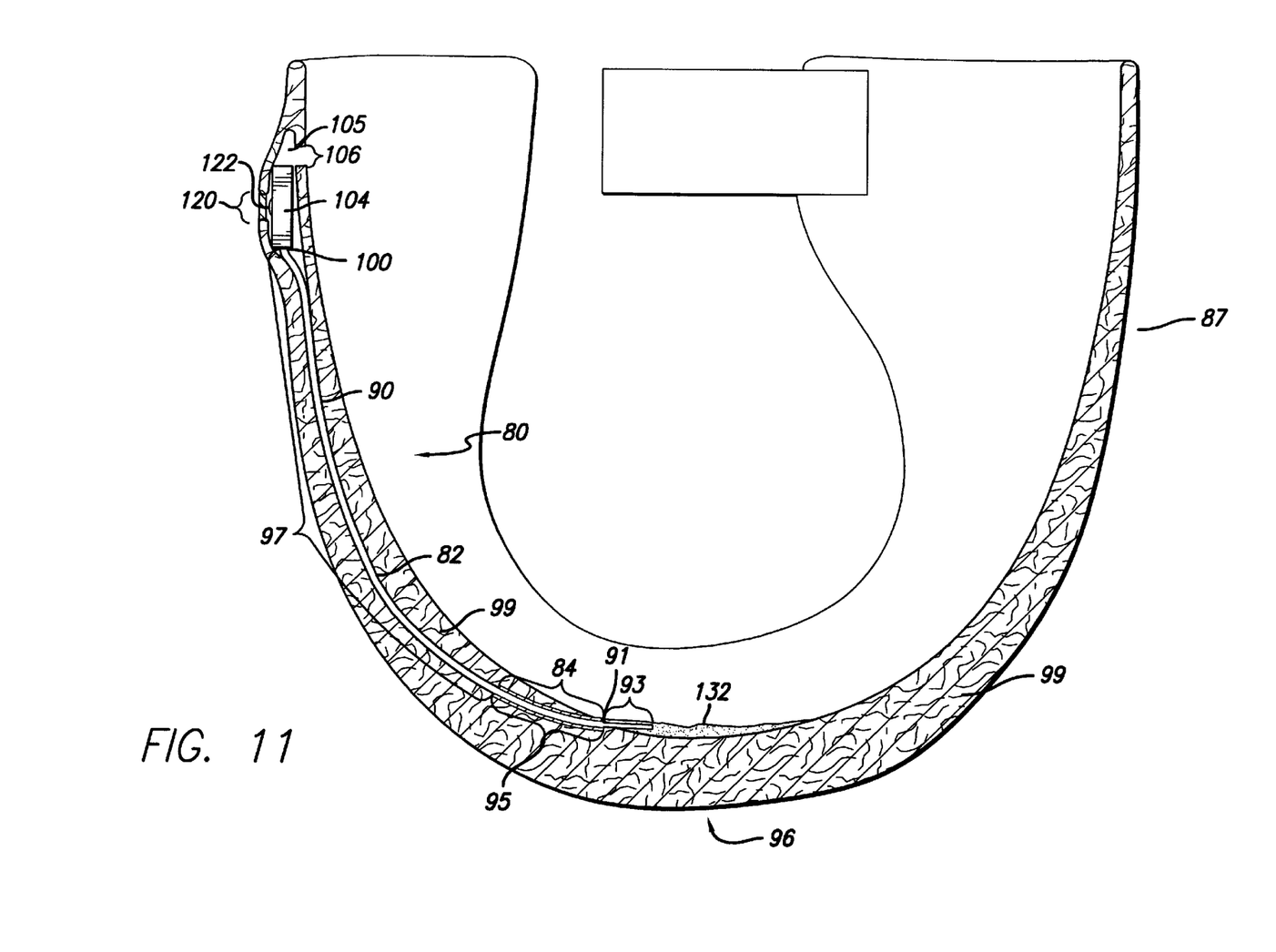
FIG. 11 is a cross-sectional view taken along section line 11—11 of FIG. 9 showing a reusable alarm signal unit removably inserted in an internal pocket of an undergarment (such as a diaper) in accordance with the present invention.

In accordance with an alternative embodiment of the present invention, a moisture sensing apparatus for use in detection of urination in clothing articles such as diapers for young children and/or incontinent adults, generally referred to by a reference numeral 80, is shown integrated (by the diaper manufacturer) in a diaper 86 (FIGS. 9–10) or a diaper 87 (FIG. 11). Integrated moisture sensing apparatus 80 comprises a disposable pouch-like diaper insert 84 partially enclosing a disposable moisture sensor 82 which is essentially identical in construction, function and configuration as disposable moisture sensor 22 of FIGS. 1–8. Diaper insert 84 is similar in construction and function to diaper insert 24 of FIGS. 1–8, i.e. it is preferably made of dental-bib-type paper which has a waterproof plastic inner wall (not shown) as diaper insert 24, except that it is generally rectangular in shape and preferably much shorter in length than diaper insert 24 as it is intended to envelop completely only the portion of moisture sensor 82 supplied (on one side) with a respective tortuous conductive ink pattern.

Specifically, disposable moisture sensor 82 may be constructed from an elongated generally rectangular strip of a highly efficient capillary liquid transfer wick material 90 (FIGS. 9–11) designed to enhance absorption, retention and transfer of liquid by capillary attraction. A wick of this type is commercially available from Filtrona Richmond, Inc. of Richmond, Va. under the trademark name TRANSPAD®.

Wick strip 90 comprises a substantially short first portion 93 (FIGS. 10–11) which protrudes out of a first open end 91 (FIGS. 10–11) of diaper insert 84 and is intended for placement in a crotch area 94 of diaper 86 (FIG. 10) or in a crotch area 96 of diaper 87 (FIG. 11) to allow rapid transfer of moisture (such as from urination) 130 (FIG. 10) or 132 (FIG. 11), respectively, by capillary attraction to an adjacent second portion 95 (FIGS. 9–11) of similar length relative to first portion 93. Second portion 95 preferably has a tortuous conductive ink pattern 88 (FIG. 9) screen printed on one side substantially along its entire length and is fully enclosed by the waterproof inner wall of diaper insert 84 to prevent undesirable loss of transferred (via first portion 93) moisture (urination) to a highly absorbent diaper padding 98. Second portion 95 may be adhesively attached via its opposite non-screen printed side to the inner waterproof wall of diaper insert 84 before integration within the diaper padding. Other securing means may be utilized, provided such other means do not depart from the intended purpose of the present invention.

Figure 9:
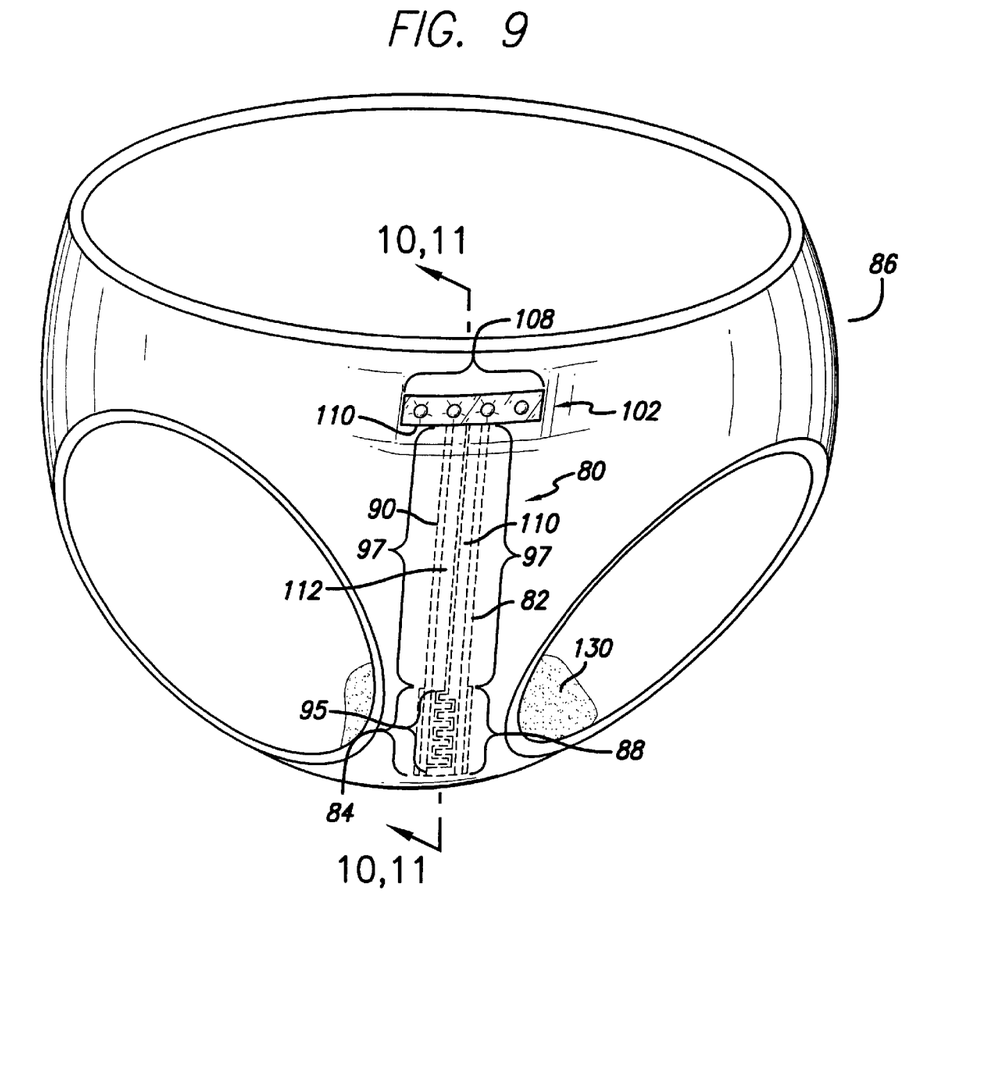
FIG. 9 is a perspective view of an alternative embodiment of the present invention.
Figure 10:
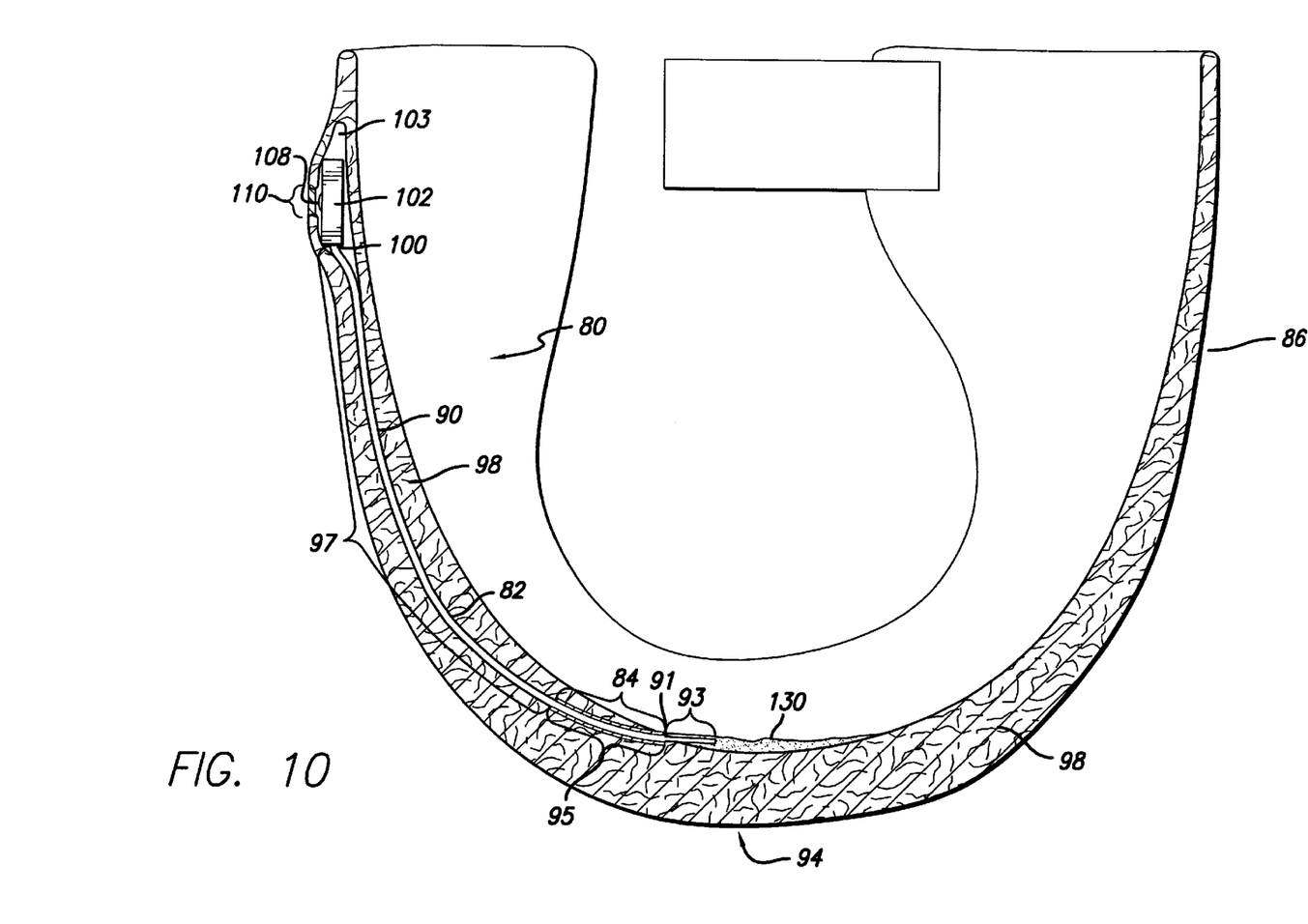
FIG. 10 is a cross-sectional view taken along section line 10—10 of FIG. 9 showing a disposable alarm signal unit integrated in an undergarment (such as a diaper) in accordance with the present invention.

Wick strip 90 further comprises a substantially long (relative to second portion 95) portion 97 (FIGS. 9–11) disposed adjacent to second portion 95 and preferably having a pair of elongated generally parallel conductive ink bands 110, 112 (FIG. 9) screen printed on the same side as second portion 95 and intended to function essentially as conductive bands 44, 46 of FIGS. 6–7. As generally illustrated in FIG. 9, conductive ink bands 110, 112 terminate on one side in tortuous conductive ink pattern 88 and are coupled electrically on the opposite side to an alarm signal unit. Third portion 97 is not enveloped by diaper insert 84 (FIGS. 9–11) but is instead fully integrated within padding 98 of diaper 86 (FIG. 10) or padding 99 of diaper 87 (FIG. 11).

Alternatively, the present invention may be practiced if diaper insert 84 is modified to fully enclose third portion 97 (not shown). Third portion 97 may be adhesively secured within padding 98 of diaper 86 (FIG. 10) or padding 99 of diaper 87 (FIG. 11) via its opposite non-screen printed side. Other securing means may be utilized, provided such other means do not depart from the intended purpose of the present invention. Third portion 97 preferably has an end 100 adapted for electrical coupling to a relatively compact, portable and disposable alarm signal unit 102 incorporated (by the diaper manufacturer) in an integral closed pocket 103 of diaper 86 (FIG. 10) or to a relatively compact, portable and re-usable alarm signal unit 104 removably inserted in an integral open pocket 105 of diaper 87 (FIG. 11). Pocket 105 is preferably provided with an opening 106 (FIG. 11) on the interior side of diaper 87 to allow insertion and/or removal of re-usable alarm signal unit 104.

As further shown in FIG. 9, disposable alarm signal unit 102 is essentially a visual-type alarm in that it is preferably provided with a series of color-coded lights 108 which are visible through a transparent window 110 (FIGS. 9, 10) provided on the front side of the waistline portion of diaper 86. Color-coded lights 108 may be activated in sequence upon detection of moisture (urination) in diaper 86 to alert a caregiver that a diaper change is in order. Transparent window 110 may be formed by incorporating a suitable transparent plastic material in the waistline portion of diaper 86 or by utilizing a transparent plastic material (at least on the front) to form the waistline of the diaper at the time of manufacture. Other means of providing a transparent window on a front side or on any other side in the waistline portion of the diaper may be used provided such other means fall within the scope of the present invention.

In a similar fashion, the waistline portion of diaper 87 is also provided on the front with a transparent window 120 (FIG. 11) for viewing a series of color-coded lights 122 (FIG. 11) provided on re-usable alarm signal unit 104. Window 120 may be constructed in the above-described manner.

A person skilled in the art would also appreciate that the above-described novel moisture sensing apparatus may be adapted for use in other applications as long as such adaptations do not deviate from the intended purpose of the present invention. Also, other components and/or configurations may be utilized in the above-described embodiments, provided such components and/or configurations fall within the scope of the present invention.

While the present invention has been described in detail with regards to the preferred embodiments, it should be appreciated that various modifications and variations may be made in the present invention without departing from the scope or spirit of the invention. In this regard it is important to note that practicing the invention is not limited to the applications described hereinabove. Many other applications and/or alterations may be utilized provided such other applications and/or alterations do not depart from the intended purpose of the present invention.

It should be appreciated by a person skilled in the art that features illustrated or described as part of one embodiment can be used in another embodiment to provide yet another embodiment such that the features are not limited to the specific embodiments described above. Thus, it is intended that the present invention cover such modifications, embodiments and variations as long as they come within the scope of the appended claims and their equivalents.

What is claimed is:

1. An apparatus for sensing moisture at a first location, comprising:
   (a) a strip of highly efficient capillary liquid transfer wick material having first and second ends and a first portion at said first end and adapted to be disposed at said first location, a second portion disposed adjacent said first portion and a third portion disposed at said second end adjacent said second portion adapted to efficiently absorb and transfer moisture via capillary attraction from said first location to a second location disposed in close proximity to said first location, said first and second portions of said strip being short relative to said second portion; and
   (b) means for quickly sensing transferred moisture at said second location and triggering a corresponding alarm signal including at least two spaced apart conductive ink bands disposed on a first side of said second and third portions of said strip of wick material; and
   (c) a waterproof pouch for enclosing said second portion.

2. The apparatus of claim 1, wherein said waterproof pouch comprises an opening at a first end and a pocket at a second end for removably receiving a portable alarm unit containing an alarm signaling circuit, said first portion of said wick strip protruding from said first end of said pouch.

3. The apparatus of claim 2, further comprising means for increasing the moisture contact surface area at said second location.

4. The apparatus of claim 3, wherein said moisture contact surface area increasing means includes a terminal tortuous path for said conductive ink bands disposed on said first side of said second portion in close proximity to said first portion.

5. The apparatus of claim 2, wherein said waterproof pouch is adapted for coupling to a clothing article on which said first location is defined.

6. The apparatus of claim 1, wherein said quick moisture sensing means includes at least two spaced apart conductive ink bands screen-printed on said first side of said third portion of said wick strip, a tortuous path for at least two spaced apart conductive ink bands screen-printed on said first side of said second portion of said wick strip in close proximity to said first portion and connected to said conductive ink bands on said third portion, a pouch for waterproofing at least said second portion, and an alarm signaling circuit operatively coupled to said conductive ink bands on said third portion.

7. The apparatus of claim 6, wherein said pouch comprises an opening at a first end, said first portion of said wick strip protruding from said first end.

8. The apparatus of claim 6, wherein said pouch and said third portion of said wick strip are adapted for integrating with a clothing article on which said first location is defined.

9. The apparatus of claim 8, wherein said clothing article is adapted to receive a disposable alarm unit containing said alarm signaling circuit.

10. The apparatus of claim 8, wherein said clothing article is adapted to receive a reusable alarm unit containing said alarm signaling circuit.

11. A method for quickly sensing moisture from urination in a diaper, said method comprising the steps of:
   (a) screen-printing a pair of spaced apart conductive ink bands with a terminal tortuous conductive ink pattern on a strip of highly efficient capillary liquid transfer wick material leaving a non-conductive front wick portion in close proximity to the tortuous conductive ink pattern;
   (b) providing a pouch adapted to waterproof at least the tortuous conductive ink pattern portion of the wick strip;
   (c) operatively coupling an alarm signaling circuit to the screen-printed conductive ink bands on the wick strip; and
   (d) disposing the non-conductive front wick portion in a diaper crotch area.

* * * * *